(12) United States Patent
Gerster

(10) Patent No.: US 8,006,400 B2
(45) Date of Patent: Aug. 30, 2011

(54) BABY SCALES

(75) Inventor: Stephan Gerster, Wachtberg-Pech (DE)

(73) Assignee: Soehnle Professional GmbH & Co. KG, Backnang (DE)

( * ) Notice: Subject to any disclaimer, the term of this patent is extended or adjusted under 35 U.S.C. 154(b) by 0 days.

(21) Appl. No.: 12/435,789

(22) Filed: May 5, 2009

(65) Prior Publication Data

US 2010/0005675 A1    Jan. 14, 2010

(30) Foreign Application Priority Data

May 7, 2008  (DE) .......................... 10 2008 022 681

(51) Int. Cl.
*G01G 19/50*  (2006.01)
*G01B 1/00*  (2006.01)

(52) U.S. Cl. ........................................... 33/512

(58) Field of Classification Search ............. 33/511, 33/512, 515; 177/245
See application file for complete search history.

(56) References Cited

U.S. PATENT DOCUMENTS

| | | |
|---|---|---|
| 1,275,911 A | 8/1918 | Hansen |
| 2,210,399 A | 8/1940 | Ericksen |
| 2,931,640 A | 4/1960 | Riddle, Jr. |
| D274,991 S | 8/1984 | Wirtz |
| 4,711,313 A | 12/1987 | Iida et al. |
| 4,800,973 A | 1/1989 | Angel |
| D304,308 S | 10/1989 | Morooka |
| 5,499,457 A | 3/1996 | Weiler et al. |
| 5,637,838 A * | 6/1997 | Arey et al. ................... 33/511 |
| 6,256,896 B1 | 7/2001 | Landauer |
| 6,998,543 B2 | 2/2006 | Sugrue et al. |
| 7,199,311 B1 | 4/2007 | Bruckner et al. |
| 7,235,746 B2 | 6/2007 | Williamson |
| 7,683,272 B2 * | 3/2010 | Hong ........................... 177/126 |
| 2009/0114455 A1 | 5/2009 | Mueller et al. |
| 2009/0173550 A1 | 7/2009 | Gerster |
| 2009/0294184 A1 | 12/2009 | Gerster et al. |

FOREIGN PATENT DOCUMENTS

| | | |
|---|---|---|
| DE | 29611425 U | 11/1997 |
| DE | 29616144 | 1/1998 |
| DE | 102006004961 A1 | 8/2007 |
| DE | 102006004962 A1 | 8/2007 |
| DE | 102006031950 B3 | 11/2007 |
| DE | 102006034871 A1 | 1/2008 |
| FR | 2645956 A1 | 10/1990 |
| FR | 2675255 A1 | 10/1992 |
| FR | 2708343 A1 | 2/1995 |
| WO | 2004038890 A1 | 5/2004 |
| WO | 2007087799 A1 | 8/2007 |

* cited by examiner

*Primary Examiner* — Yaritza Guadalupe-McCall
(74) *Attorney, Agent, or Firm* — Leydig, Voit & Mayer, Ltd.

(57) ABSTRACT

Baby scales include a housing, a weighing tray, a measuring device and a display. The weighing tray is disposed on the housing and configured to hold a baby. The measuring device is configured to support the weighing tray and to determine a weight of the baby. The measuring device includes at least one of an electric length measuring device configured to measure a length of the baby and an attachment mechanism configured to attach the electric length measuring device. The display is configured to show the determined weight of the baby.

15 Claims, 4 Drawing Sheets

BABY SCALES

PRIORITY CLAIM

Priority is claimed to DE 10 2008 022 681.5, filed May 7, 2008.

FIELD

The present invention relates generally to baby scales and specifically to baby scales having a housing, a weighing tray installed on the housing to hold a baby, a measuring device that supports the weighing tray and serves to determine the weight of the baby, and a display to show the determined weight.

BACKGROUND

Baby scales of the type under discussion are used in actual practice and exist in various versions. Prior baby scales have, for example, a housing with a weighing tray installed on the housing to hold a baby, whereby the weighing scales are installed on a measuring device for determining the weight of the baby. Moreover, the baby scales have a display to show the determined weight of the baby. Baby scales of the above-mentioned type are used in the private realm and also as calibrated baby scales for weighing babies in hospitals, in pediatric clinics, in doctor's offices and by midwives. The prior-art baby scales are able to reliably determine the weight of the baby who is to be weighed.

However, when it comes to baby care, it is not only important to determine the weight but also the length of the baby. In particular, taking into account a combination of the weight value with the corresponding length measurement, conclusions can be drawn about the developmental and nutritional state of the baby. For this purpose, after the babies have been weighed, they are measured with a separate measuring stick or measuring tape in a usually impractical procedure. Especially in hospitals and doctor's offices, where a large number of babies have to be taken care of at almost the same time, there is a risk that the measuring tape or measuring stick is not at hand right away or has even been misplaced. This considerably impairs the convenient care of the babies.

U.S. Pat. No. 5,499,457 describes a device for measuring the length and the weight of babies, which includes not only scales but also a length measuring device. Disadvantageously, with this type of device, no simultaneous and sufficiently accurate measurements of length and weight are possible.

Baby scales are also used whose weighing surface has a measuring tape glued onto it. These scales especially have the drawback that the measuring tape is hard to read when the baby is lying on it or next to it. Moreover, these scales have the disadvantage that the measured values cannot be further processed or stored in electronic form.

SUMMARY

It is an aspect of the present invention to provide baby scales that allow a convenient, precise and simultaneous measurement of a baby.

In an embodiment, the present invention provides baby scales including a housing, a weighing tray, a measuring device and a display. The weighing tray is disposed on the housing and configured to hold a baby. The measuring device is configured to support the weighing tray and to determine a weight of the baby. The measuring device includes at least one of an electric length measuring device configured to measure a length of the baby and an attachment mechanism configured to attach the electric length measuring device. The display is configured to show the determined weight of the baby.

BRIEF DESCRIPTION OF THE DRAWINGS

There are various possibilities to configure and refine the teaching of the present invention. In this context, reference is made to the explanation below of an embodiment of the invention with reference to the drawing. In conjunction with the explanation of the embodiment of the invention with reference to the drawing, generally embodiments and refinements of the teaching will also be explained. The following is shown in the drawing.

DETAILED DESCRIPTION

Figure 1:
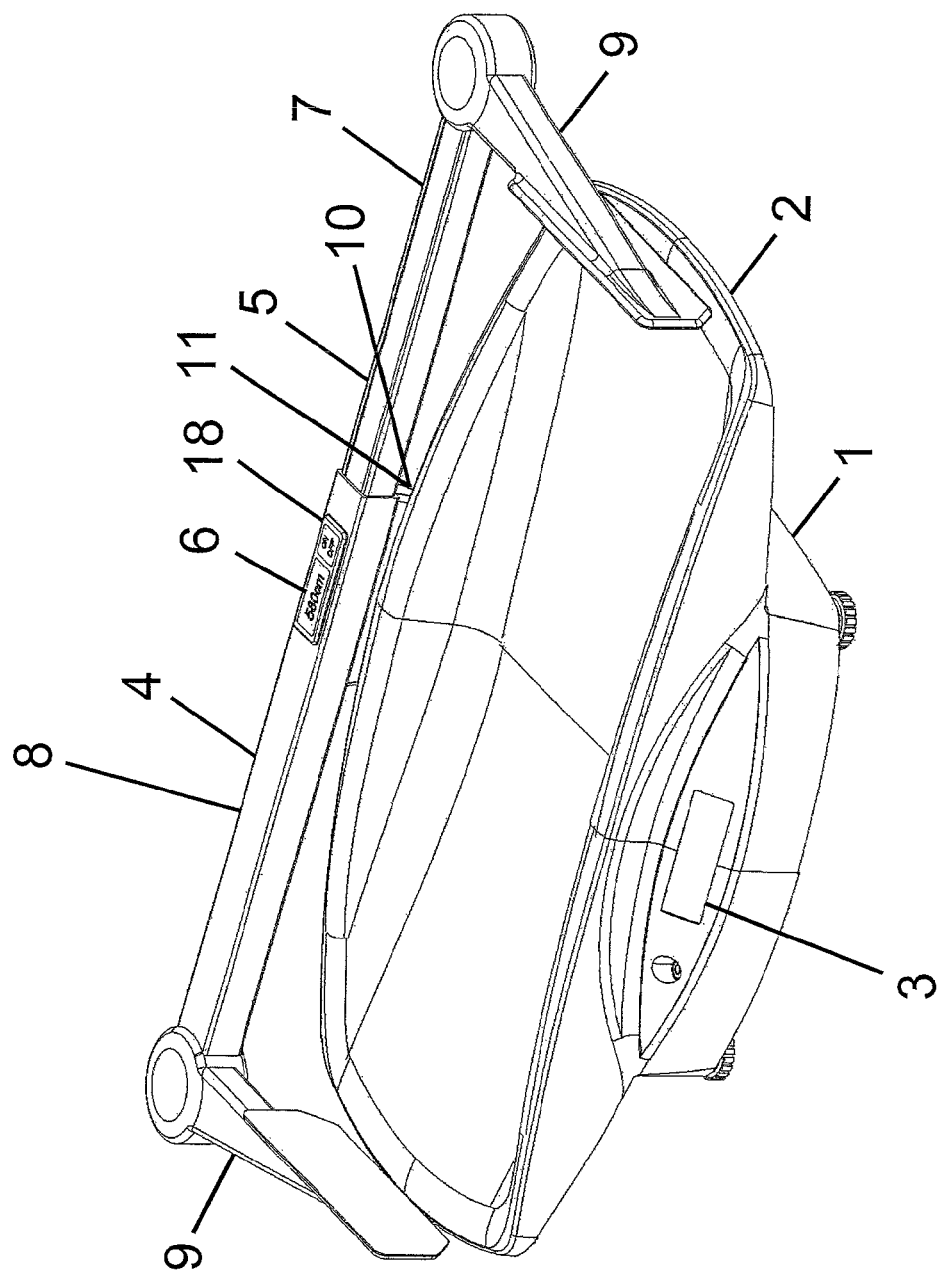
FIG. 1 a schematic and perspective view of an embodiment of baby scales according to the invention, with a digital measuring slider, FIG. 2 a schematic and perspective view of the embodiment shown in FIG. 1, seen from the back and with the length measuring device removed, which in this case is an analog measuring slider, FIG. 3 a schematic and perspective view of the embodiment shown in FIG. 2, with an attached length measuring device, and FIG. 4 a schematic and perspective view of two different length measuring devices.

According to the invention, an embodiment provides baby scales that are characterized in that the measuring device additionally, directly or indirectly, has an electric length measuring device to measure the baby, and/or an attachment mechanism to attach an electric length measuring device for measuring the baby.

Due to the fact that the length measuring device can be installed on the housing or to the weighing tray, it is possible to not only weigh the baby who is being cared for but also to measure its body length, virtually at the same time. These two pieces of information about the weight and length of the baby make it easy to draw conclusions about the developmental and nutritional state of the baby and, for example, to appropriately plan the further feeding regimen of the baby.

In the manner according to the invention, it has been recognized that, with prior-art devices, a precise weight measurement becomes impossible if the sensors or the measuring arms of mechanically separate length measuring devices are in contact with the baby who is to be weighed. Therefore, with the scales according to the invention, it is provided that the measuring device for determining the weight of the baby, directly or indirectly, also supports the length measuring device that likewise gets weighed. However, the fact that the length measuring device is likewise weighed is not a problem because the known weight of the length measuring device—like, for instance, the weight of the weighing tray as well—can be automatically subtracted from the measured result, or because the baby scales have a tare function that sets the measuring device to zero before the measurement is started.

In an embodiment, it is provided that the length measuring device is configured as a measuring slider. This ensures not only a simple construction but also a simple handling of the length measuring device by a user.

In an especially convenient manner, the measuring slider can be configured as a digital measuring slider. This allows a particularly simple and exact acquisition of the measured length values. In order to display the ascertained measured values simply and without problems, the measuring slider can have a digital display. The ascertained measured values can be read off especially easily and precisely to at least one decimal point position. As an alternative or in addition, it can also have an analog display, for example, in order to allow a simple reading of the acquired measured values.

In another structurally simple manner, the measuring slider can have two elements that can slide into each other. In concrete terms, the elements can slide into each other telescopically. Simple elements can be polygonal pipes or polygonal rods whose angular shape reliably prevents them from twisting relative to each other in an undesired manner.

Appropriate units of length or a length scale can be marked on the elements that slide into each other. With such a length scale, even before the actual measurement, at least a rough estimate can be made as to the length of the baby.

With an eye towards an especially precise length measurement, the outer ends of the elements can each have a stop element that can pivot relative to the element in question. In order to measure the length of a baby, the stop element should be placed into its measuring position, which is essentially a position that is perpendicular to the elements or to the individual element. When the length measuring device is not being used and/or in order to position the baby on the scales without hindrance by the length measuring device, the stop elements can be pivoted away from the baby scales or from the weighing tray, whereby, in their pivoted-away position, the stop elements can, so to speak, form an extension of the elements that can slide into each other.

In an advantageous manner, the length measuring device can be attached and detached in the manner of a retrofitted part. Thus, if desired, baby scales can be purchased without a length measuring device to start with and a length measuring device can be retrofitted if necessary. In any case, the baby scales can already be pre-configured for such a retrofitting. For cleaning or transporting purposes as well, it is practical if the length measuring device can be removed.

With an eye towards a secure installation of the length measuring device on the housing or on the weighing tray, the length measuring device can have an additional attachment mechanism that can be arranged on the housing or on the weighing tray. Here, various versions of the attachment mechanism are conceivable.

In another structurally simple manner, the additional attachment mechanism can have a spring-preloaded clamp. Such a clamp can be used to easily clamp the length measuring device onto the housing or onto the weighing tray. Such a clamp can be configured in such a way that two clamp jaws spread when the clamp is actuated, and, due to the spring action, these clamp jaws move towards each other when the clamp is released, and they can, for example, grip an edge of the weighing tray. Such a clamp makes it especially easy to arrange the length measuring device on the housing or on the weighing tray.

As an alternative to this, in another structurally simple manner, the additional attachment mechanism can have an insertion element or a receptacle. Such an insertion element or such a receptacle can interact in a simple manner with a corresponding receptacle or a corresponding insertion element of the housing or weighing tray, in order to provide an especially secure positioning and an especially precise arrangement of the length measuring device on the housing or on the weighing tray.

In an especially practical and convenient manner, the additional attachment mechanism can have an electric contact to supply power to the length measuring device via the baby scales and/or to transmit signals between the length measuring device and the baby scales. If an electric contact is provided to supply power, the power can be supplied to the length measuring device—for example, in a version of the length measuring device as a digital measuring slider—in an especially convenient, reliable and simple manner via the power supply of the baby scales. The baby scales can be provided with power either by means of a battery or by means of a mains connection. Consequently, a separate battery or a separate mains connection is not needed for the length measuring device.

In highly precise baby scales, it is provided that the length measuring device has its own power supply that is electrically separate from the power supply of the measuring device. In particular, it can be provided that the measuring device, directly or indirectly, mechanically has its own power supply. This effectively prevents part of the weight to be measured from being missed by the measuring device since it is exerted on the supply cables, or else it prevents parts of the supply cables from inadvertently being weighed along with the baby. Both of these scenarios would falsify the weight measurement. Before this backdrop, as an alternative or in addition, means can be provided for a cable-free transmission of energy to the length measuring device. Here, it is possible for the length measuring device to be supplied directly with the transmitted energy or for the transmitted energy to be initially buffered, for example, in a battery.

In an especially efficient embodiment, the means for the cable-free transmission function inductively and/or capacitively. For example, it can be provided that the means for the cable-free transmission can have at least one coil.

One embodiment of an electric contact for signal transmission between the length measuring device and the baby scales allows an especially convenient operation of the baby scales and of the length measuring device. For example, measured data acquired by means of the length measuring device or ascertained measured length values can be transmitted to the baby scales and displayed on the display of the baby scales—optionally together with an ascertained weight value. A cost-effective aspect is that a separate display for the length measuring device would not be necessary in this case. As an alternative or in addition to this, it would be conceivable to transmit signals from the baby scales to the length measuring device, for example, in order to transmit control data for the length measuring device.

In order to ensure an especially secure arrangement of the length measuring device on the housing or on the weighing tray, the attachment mechanism can have latching and/or locking means. For example, when the length measuring device is being attached, a latching tab can engage with the housing or with the weighing tray, so as to prevent accidental removal of the length measuring device from the housing or weighing tray. However, such a latching tab can be disengaged again in a simple manner—by an intentional action of a user—so that it remains possible to remove the length measuring device from the housing or weighing tray in a simple manner.

With an eye towards a simple and secure arrangement of the length measuring device on the housing or on the weighing tray, the housing or weighing tray can have an attachment mechanism for attaching the length measuring device. Here, in a simple manner, the attachment mechanism can have a receptacle or an insertion element that can interact with a corresponding insertion element or with a corresponding receptacle on the length measuring device.

In an especially practical and convenient manner, the attachment mechanism can have an electric contact to supply power to the length measuring device via the baby scales and/or to transmit signals between the length measuring device and the baby scales. As far as the advantages and functionality of baby scales having such an electric contact are concerned, in order to avoid repetitions, reference is hereby made to the description of the advantages of such an electric contact in conjunction with the above-mentioned attachment mechanism of the length measuring device.

In order to reliably arrange the length measuring device on the housing or on the weighing tray, the attachment mechanism can have latching and/or locking means.

In this manner, accidental separation of the length measuring device from the housing or from the weighing tray is prevented.

Especially with an eye towards obtaining an unfalsified weight measurement, in an embodiment, the signal transmission from and/or to the length measuring device is effectuated without cables. For example, the signal transmission from and/or to the length measuring device can be effectuated via a radio connection, especially a Bluetooth connection. Such a signal transmission is independent of any attachment mechanisms. Finally, however, in an especially simple embodiment, a cable can also run from the length measuring device to the baby scales. For this purpose, appropriate insertion mechanisms can be provided. However, it is especially elegant to effectuate the signal transmission by a radio connection, as a result of which the need to lay cables and thus the above-mentioned problem of the risk of a falsification of the measuring values can be avoided.

In order to create a length measuring device that is independent of the power supply of the baby scales, the length measuring device can be operated by means of a battery.

In an especially compact embodiment of the baby scales, the housing and the weighing tray are configured so as to be an integral part. Finally, the weighing tray can be integrally shaped onto the housing or the housing can be integrally shaped onto the weighing tray.

In an especially practical manner, the weight as well as the length of the baby can be shown on the display of the baby scales. This allows an especially clear display of the data and values determined by the baby scales.

In order to further process or archive the data and/or measured values acquired by the baby scales and/or by the length measuring device, the baby scales can have a device to output the data and/or measured values acquired and/or determined by the baby scales and/or by the length measuring device. Depending on the application case, such a device can be configured to output the data and/or the measured values via a cable and/or via radio. Especially in the case of longer transmission distances between the baby scales and a processing device—for example, a personal computer—transmission via radio is especially practical since longer cables can be avoided.

In another especially convenient manner, the electronic system of the baby scales and/or of the length measuring device can be configured in such a way that that switching the baby scales over between different units of weight brings about a corresponding switching over between different units of length of the length measuring device. For example, if a user switches the unit of weight of the baby scales from kilograms to pounds, this can automatically result in a switching over of the unit of length from centimeters to inches. In the same manner, switching over the unit of length of the length measuring device can automatically result in a switching over of the unit of weight of the baby scales. An appropriate attaching can be provided here.

FIG. 1 shows a schematic and perspective view of an embodiment of baby scales according to the invention, having a housing 1, a weighing tray 2 installed on the housing 1 to hold a baby, a measuring device (not shown here) that supports the weighing tray 2 and serves to determine the weight of the baby, and a display 3 to show the determined weight. With an eye towards achieving convenient care of the baby employing a structurally simple means, a length measuring device 4 for the baby is installed on the housing 1 or to the weighing tray 2.

The baby scales shown in FIG. 1 are standing on a substrate (not shown here) and they allow the determination of the weight of a baby to be measured as well as the determination of its length. The attached length measuring device 4 is configured as a digital measuring slider 5. The measuring slider 5 has a digital display 6 so that the measured length of the baby can be read off. Concretely speaking, the measuring slider 5 has two elements 7 and 8 that can slide into each other. The outer ends of the elements 7 and 8 each have a stop element 9 that can pivot relative to the corresponding element 7 and 8. When the length measuring device 4 is not being used and/or in order to position the baby on the weighing tray 2 without hindrance, the stop elements 9 can be pivoted away from the baby scales.

The length measuring device 4 can be arranged on the baby scales and detached from them in the manner of a retrofitted component. With an eye towards attaining a secure installation of the length measuring device on the baby scales, the length measuring device 4 has an additional attachment mechanism 10. Concretely speaking, the attachment mechanism 10 has an insertion element 11.

Figure 2:
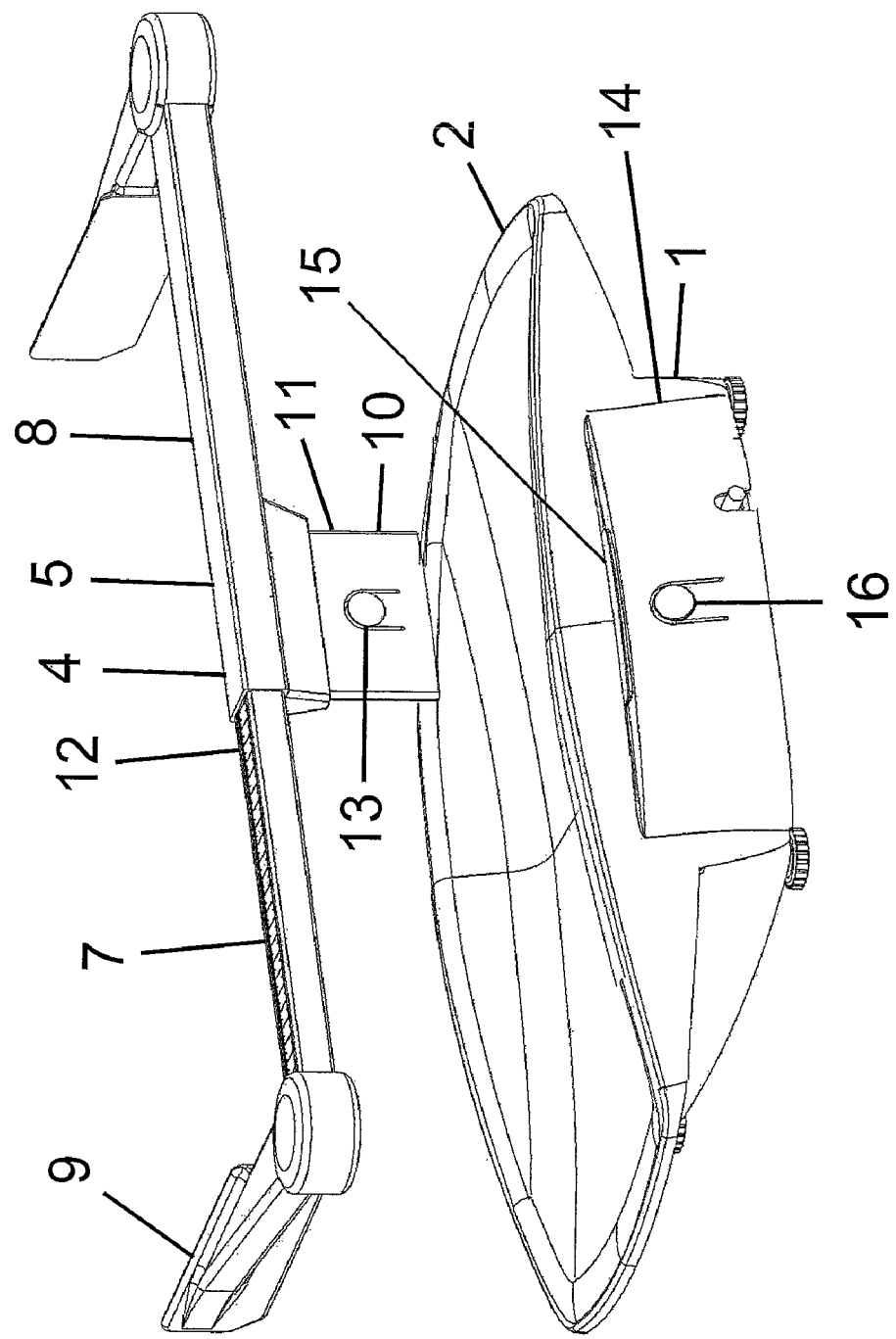
Figure 3:
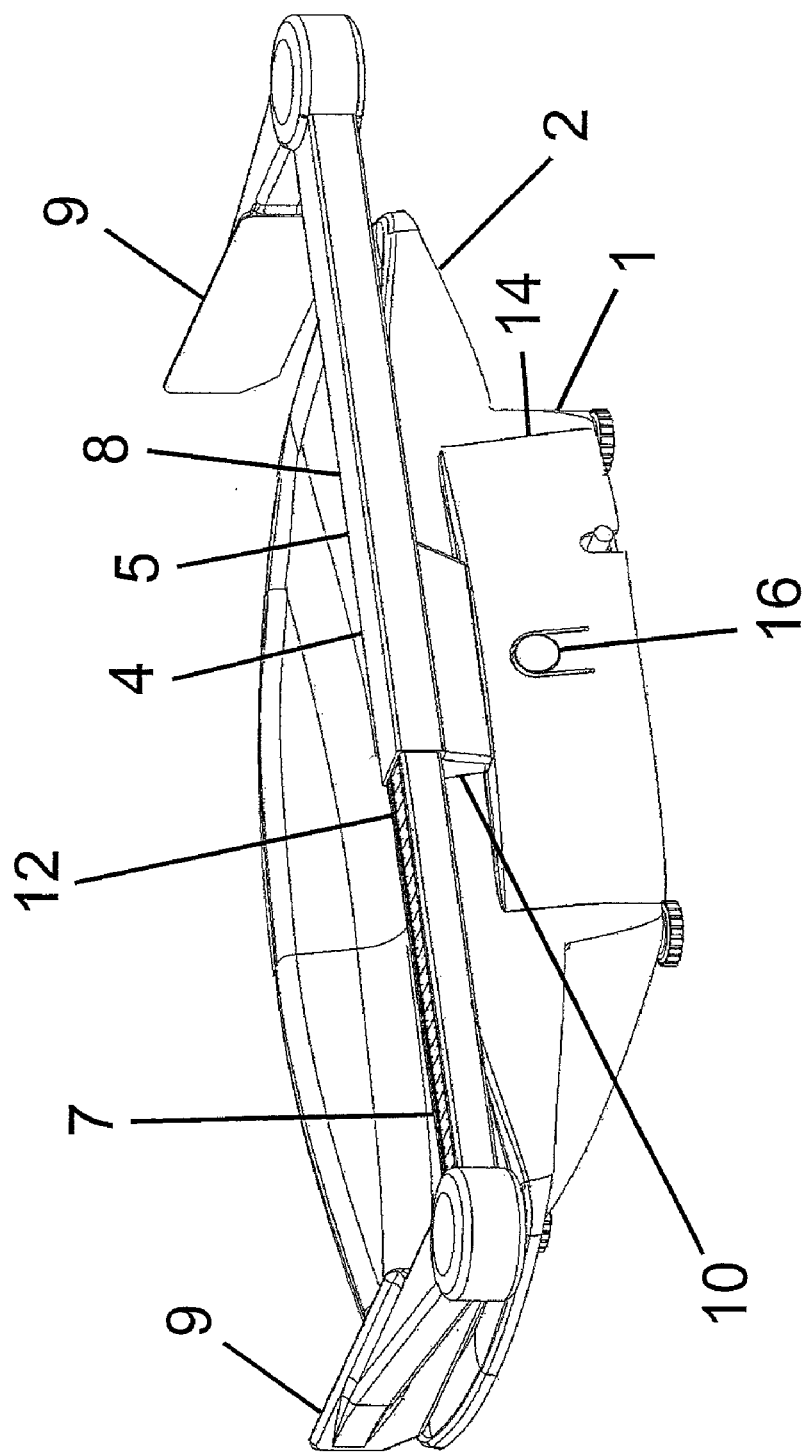

In schematic and perspective views—seen from the back of the baby scales—FIGS. 2 and 3 show the unattached and attached states of the length measuring device 4. In FIGS. 2 and 3, the length measuring device 4 is configured as an analog length measuring device 4 having an analog display 12. The analog display 12 has a length scale.

The additional attachment mechanism 10 has a latching and locking means 13 on the insertion element 11, said this latching and locking means 13 making it possible to latch and/or lock the length measuring device 4 onto the baby scales.

For this purpose, the housing 1 has an attachment mechanism 14 to attach the length measuring device 4. The attachment mechanism 14 has a receptacle 15 into which the insertion element 11 of the length measuring device 4 can be inserted, as is shown in FIG. 3. The attachment mechanism 14 also has latching and/or locking means 16 that interact with the latching and/or locking means 13 of the attachment mechanism 11.

The latching and/or locking means 16 have a spring element that engages into a recess of the latching and locking means 13 of the length measuring device 4.

Figure 4:
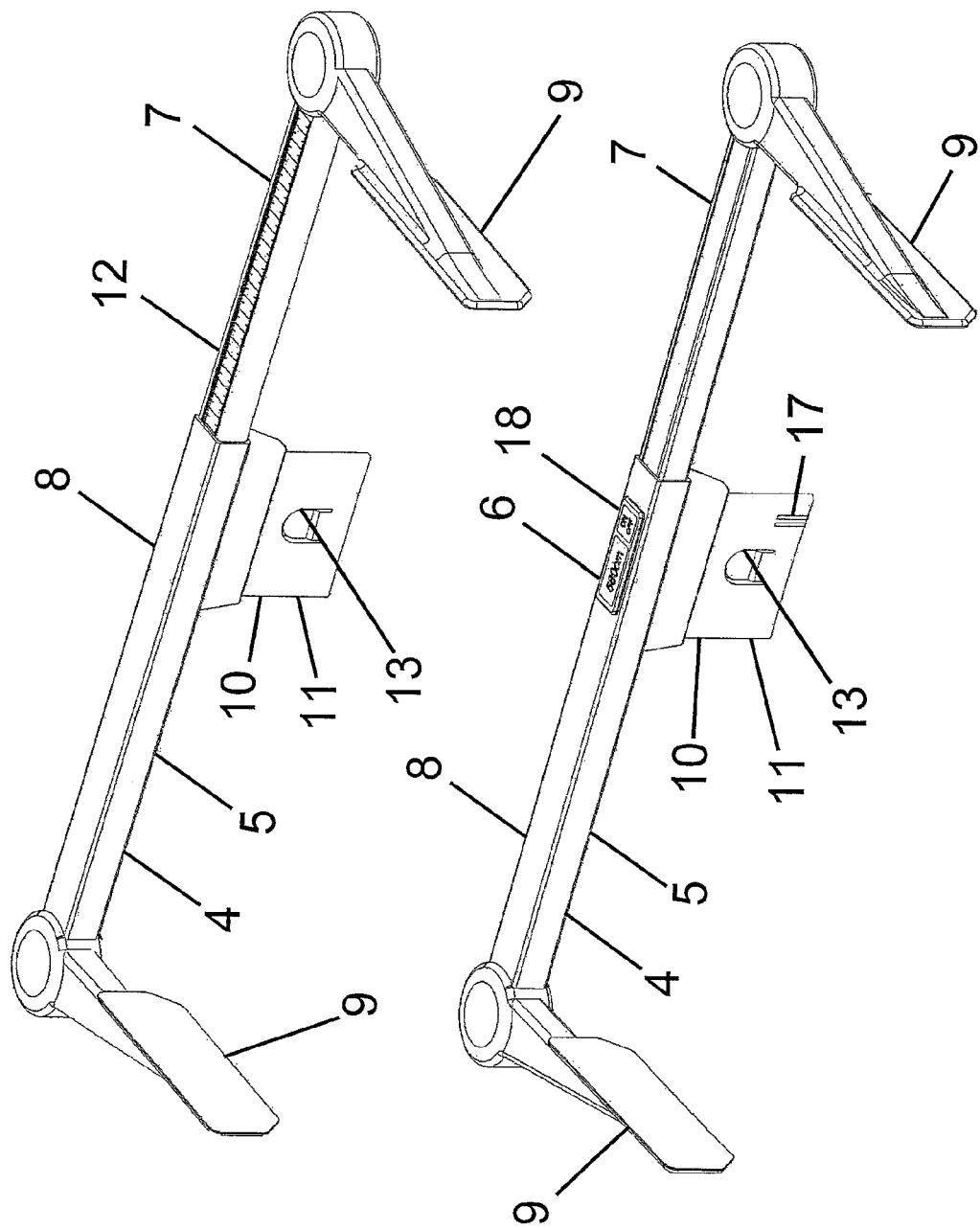

FIG. 4 shows a schematic and perspective view of two different measuring sliders 5 that, on the one hand, have an analog display 12 and, on the other hand, a digital display 6. The length measuring device 4 shown in the lower section of FIG. 4 has an electric contact 17 on the insertion element 11 in order to supply power to the length measuring device 4 via the power supply of the baby scales. A separate power supply for the digital display 6, for example, via a battery, is not needed here. Via the electric contacts 17, signals can also be transmitted between the length measuring device 4 and the baby scales or the electronic system of the baby scales. In this manner, measured values or measured data acquired with the length measuring device 4 can be transmitted to the baby scales, or else control signals can be transmitted from the baby scales to the length measuring device 4.

An ON/OFF switch 18 is provided adjacent to the digital display 6 to turn the digital display 6 on and off.

As far as additional embodiments of the baby scales according to the invention are concerned, in order to avoid repetitions, reference is hereby made to the general part of the description as well as to the accompanying claims.

Finally, it should be explicitly pointed out that the embodiment of the baby scales according to the invention described above serves merely to elucidate the claimed teaching, but by no means limits the claimed teaching to this embodiment.

LIST OF REFERENCE NUMERALS

1 housing
2 weighing tray
3 display
4 length measuring device
5 measuring slider
6 digital display
7 element
8 element
9 stop element
10 additional attachment mechanism
11 insertion element
12 analog display
13 latching and locking means
14 attachment mechanism
15 receptacle
16 latching and locking means
17 electric contact
18 ON/OFF switch

The invention claimed is:

1. Baby scales comprising:
a housing;
a weighing tray disposed on the housing and configured to hold a baby;
a measuring device configured to support the weighing tray and to determine a weight of the baby, wherein the measuring device includes an electric length measuring device configured to measure a length of the baby and an attachment mechanism configured to attach the electric length measuring device to the housing, wherein the electric length measuring device includes at least one of a measuring slider and a digital measuring slider, the measuring slider including a first element slideable into a second element, wherein the first element includes at least one first outer end and the second element includes at least one second outer end, the at least one first outer end having a stop element pivotable relative to the first element and the at least one second outer end having a stop element pivotable relative to the second element; and a display disposed on the housing and configured to show the determined weight of the baby.

2. The baby scales as recited in claim 1, wherein the electric length measuring device is attachable and detachable as a retrofitted part.

3. The baby scales as recited in claim 1, wherein the electric length measuring device includes an additional attachment mechanism disposable on at least one of the housing and the weighing tray.

4. The baby scales as recited in claim 3, wherein at least one of the attachment mechanism and the additional attachment mechanism includes an electric contact configured to at least one of supply power to the electric length measuring device through the baby scale and transmit a signal between the electric length measuring device and the baby scale.

5. The baby scales as recited in claim 1, wherein the electric length measuring device includes a power supply that is electrically separate from a power supply of the measuring device.

6. The baby scales as recited in claim 5, wherein the measuring device is configured to directly or indirectly mechanically carry the power supply of the measuring device.

7. The baby scales as recited in claim 1, further comprising a cable-free transmission device configured to transmit energy to the electric length measuring device in a cable-free manner.

8. The baby scales as recited in claim 7, wherein the cable-free transmission device is configured to function at least one of inductively and capacitively.

9. The bay scales as recited in claim 7, wherein cable-free transmission device includes at least one coil.

10. The baby scales as recited in claim 1, wherein the electric length measuring device is configured to transmit and receive a signal without cables via at least one of a radio connection and a Bluetooth connection.

11. The baby scales as recited claim 1, wherein the housing and the weighing tray are integral with each other.

12. The baby scales as recited in claim 1, wherein the display is configured to show the length of the baby.

13. The baby scales as recited in claim 1, further comprising an output device configured to output at least one of data and measured values, the data and measured values being at least one of acquired and determined by at least one of the measuring device and the electric length measuring device.

14. The baby scales as recited in claim 1, further comprising an electronic system configured to switch the electric length measuring device to a different unit of length upon a switching of the baby scales to a different unit of weight.

15. The baby scale as recited in claim 1, wherein the electric length measuring device includes an electronic system configured to switch the electric length measuring device to a different unit of length upon a switching of the baby scales to a different unit of weight.

* * * * *